(12) United States Patent
Suzuki et al.

(10) Patent No.: US 7,342,036 B2
(45) Date of Patent: Mar. 11, 2008

(54) ISOXAZOLE DERIVATIVES AND PROCESS FOR PRODUCING THE SAME

(75) Inventors: Keisuke Suzuki, Kanagawa (JP);
Jeffrey W. Bode, Tokyo (JP)

(73) Assignee: Japan Science and Technology Agency (JP)

( * ) Notice: Subject to any disclaimer, the term of this patent is extended or adjusted under 35 U.S.C. 154(b) by 547 days.

(21) Appl. No.: 10/932,856

(22) Filed: Sep. 2, 2004

(65) Prior Publication Data
US 2005/0026978 A1 Feb. 3, 2005

Related U.S. Application Data

(63) Continuation of application No. PCT/JP02/13641, filed on Dec. 26, 2002.

(30) Foreign Application Priority Data
Mar. 8, 2002 (JP) ............... 2002-063588

(51) Int. Cl.
*C07D 261/20* (2006.01)
(52) U.S. Cl. .................. 514/379; 548/241
(58) Field of Classification Search ........ 514/379; 548/241
See application file for complete search history.

(56) References Cited

FOREIGN PATENT DOCUMENTS

| EP | 401779 A | 12/1990 |
|----|----------|---------|
| EP | 474012 A1 | 3/1992 |
| GB | 2 284 600 A | 6/1995 |

OTHER PUBLICATIONS

Easton, C.J. et al., Reversal of Regiochemistry in the Synthesis of Isoxazoles by Nitrile Oxide Cycloadditions, Tetrahedron Letters, 1994, vol. 35, No. 21, pp. 3589 to 3592, formula 3a, scheme 1.

"Electrochemical and yeast-catalysed ring-opening of isoxazoles in the synthesis of analogue of the herbicide Grasp®" by Easton et al., Journal of the Chemical Society, Perkin Transactions 1, vol. 10, 2001, pp. 1168-1174.
Supplementary European Search Report for EP 02 79 2015 completed Oct. 19, 2005.

*Primary Examiner*—Kamal A. Saeed
(74) *Attorney, Agent, or Firm*—Darby & Darby

(57) ABSTRACT

The present invention provides isoxazole derivatives represented by the following formula (I):

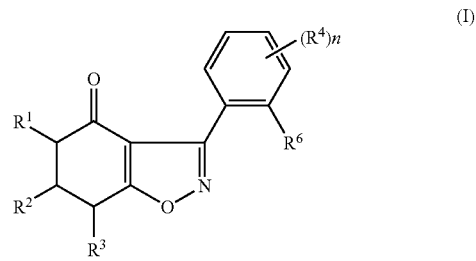

(wherein $R^1$ represents a hydrogen atom, $C_1$-$C_{20}$ hydrocarbon group or —C(=O)OR$^{1a}$ (wherein $R^{1a}$ represents a $C_1$-$C_{10}$ alkyl group, etc.); $R^2$ and $R^3$ represent a hydrogen atom, halogen atom, hydroxy group, $C_1$-$C_{20}$ alkyl group or $C_6$-$C_{20}$ aryl group, etc.; $R^4$ represents a hydrogen atom, halogen atom, hydroxy group, cyano group, nitro group, amino group, $C_1$-$C_{20}$ hydrocarbon group, $C_1$-$C_{10}$ alkoxy group, $C_1$-$C_{10}$ acyl group, 5- to 7-membered heterocyclic group, etc.; $R^5$ represents a hydrogen atom, halogen atom, hydroxy group, optionally substituted $C_1$-$C_{20}$ hydrocarbon group, $C_1$-$C_{20}$ alkoxy group, 5- to 7-membered heterocyclic group, etc.; and, n represents 0, 1, 2, 3 or 4), and a process of producing the same. The compounds are useful as intermediates for synthesis of pharmaceutical compounds, agricultural chemicals, dye compounds, etc. having the isoxazole skeleton.

1 Claim, No Drawings

ISOXAZOLE DERIVATIVES AND PROCESS FOR PRODUCING THE SAME

CROSS REFERENCE TO RELATED APPLICATIONS

This application is a continuation of International Patent Application Serial No. PCT/JP02/13641, filed Dec. 26, 2002, which published in Japanese on Sep. 18, 2003 as WO 03/076419, claiming priority of Japanese Patent Application Serial No. 63588/2002, filed Mar. 8, 2002, and is incorporated herein by reference in its entirety.

TECHNICAL FIELD

The present invention relates to isoxazole derivatives and a process of producing the same. More particularly, the present invention relates to intermediates useful for synthesis of pharmaceutical compounds, agricultural chemicals, dye compounds, etc. having the isoxazole skeleton, and a process of producing the same.

BACKGROUND ART

Coleophomones A and B, which are represented by formulae (A) and (B) below, respectively, are naturally occurring substances having a transglycosylase activity and are compounds useful as antibacterial agents.

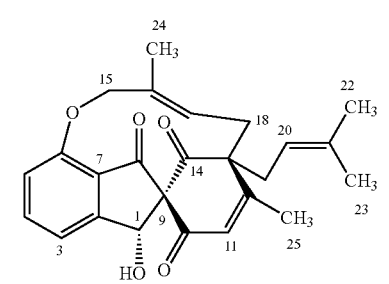

(A)

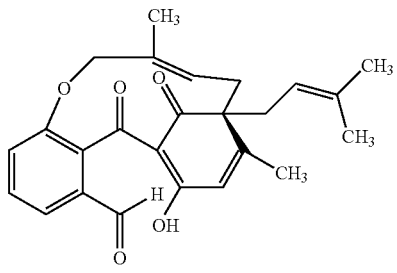

(B)

These coleophomones A and B are obtained by incubating *Coleophoma* sp. (MF6338). As shown by the formulae (A) and (B) described above, however, these compounds have a novel cyclic structure and thus, their chemical synthesis is unknown yet.

Accordingly, intermediates for synthesis of pharmaceutical compounds, agricultural chemicals, dye compounds, etc., including compounds having such a complicated structure as well as a process of producing the intermediates have been desired.

DISCLOSURE OF THE INVENTION

The present invention provides isoxazole derivatives represented by the following formula (I):

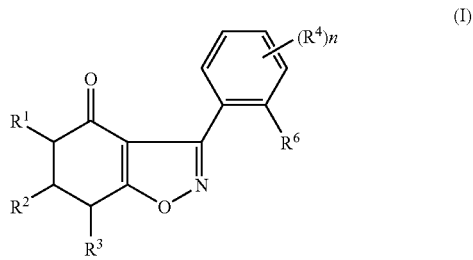

(I)

(wherein $R^1$ represents a hydrogen atom, optionally substituted $C_1$-$C_{20}$ hydrocarbon group or —C(=O)OR$^{1a}$ (wherein $R^{1a}$ is an optionally substituted $C_1$-$C_{10}$ alkyl group, optionally substituted $C_2$-$C_{10}$ alkenyl group or optionally substituted $C_2$-$C_{10}$ alkynyl group);

$R^2$ and $R^3$, which may be the same or different, each independently represents a hydrogen atom, halogen atom, hydroxy group, optionally substituted $C_1$-$C_{20}$ alkyl group or optionally substituted $C_6$-$C_{20}$ aryl group;

$R^4$, which may be the same or different, each independently represents a hydrogen atom, halogen atom, hydroxy group, cyano group, nitro group, optionally substituted amino group, optionally substituted $C_1$-$C_{20}$ hydrocarbon group, optionally substituted $C_1$-$C_{10}$ alkoxy group, optionally substituted $C_1$-$C_{10}$ acyl group or optionally substituted 5- to 7-membered heterocyclic group;

$R^5$ represents a hydrogen atom, halogen atom, hydroxy group, optionally substituted $C_1$-$C_{20}$ hydrocarbon group, optionally substituted $C_1$-$C_{20}$ alkoxy group or optionally substituted 5- to 7-membered heterocyclic group; and, n represents 0, 1, 2, 3 or 4).

In the general formula (I) described above, $R^1$ specifically represents a hydrogen atom, optionally substituted $C_1$-$C_{10}$ hydrocarbon group or —C(=O)OR$^{1a}$ (wherein $R^{1a}$ is an optionally substituted $C_1$-$C_4$ alkyl group, optionally substituted $C_2$-$C_4$ alkenyl group or optionally substituted $C_2$-$C_4$ alkynyl group); more specifically a hydrogen atom or $C_1$-$C_4$ alkoxycarbonyl group; and most specifically a hydrogen atom, methoxycarbonyl group or ethoxycarbonyl group.

In the general formula (I) described above, $R^2$ specifically represents a hydrogen atom, optionally substituted $C_1$-$C_4$ alkyl group, optionally substituted $C_2$-$C_4$ alkenyl group or optionally substituted $C_2$-$C_4$ alkynyl group; more specifically represents a hydrogen atom or $C_1$-$C_4$ alkyl group; and most specifically a hydrogen atom or methyl group;

In the general formula (I) described above, $R^3$ specifically represents a hydrogen atom, optionally substituted $C_1$-$C_4$ alkyl group, optionally substituted $C_2$-$C_4$ alkenyl group or optionally substituted $C_2$-$C_4$ alkynyl group; more specifically represents a hydrogen atom or $C_1$-$C_4$ alkyl group; and most specifically a hydrogen atom.

In the general formula (I) described above, specifically $R^4$ may be the same or different and each independently represents a hydrogen atom, halogen atom, hydroxy group, optionally substituted $C_1$-$C_{20}$ hydrocarbon group or optionally substituted $C_1$-$C_4$ alkoxy group; more specifically, $R^4$ may be the same or different and each independently represents a hydrogen atom, halogen atom, hydroxy group, $C_1$-$C_4$ alkyl group, $C_1$-$C_4$ alkoxy group or $C_1$-$C_4$ alkoxy-$C_1$-$C_4$ alkoxy group; and most specifically, $R^4$ may be the same or different and each independently represents a hydrogen atom, methoxy group or methoxymethoxy group.

In the general formula (I) described above, $R^5$ specifically represents a hydrogen atom, halogen atom, hydroxy group, optionally substituted $C_1$-$C_{20}$ hydrocarbon group, optionally substituted $C_1$-$C_{20}$ alkoxy group or optionally substituted 5- to 6-membered heterocyclic group; more specifically, $R^5$ represents a hydrogen atom, halogen atom, hydroxy group, $C_1$-$C_4$ alkoxy group or 6-membered heterocyclic group containing 1 or 2 oxygen atoms; and most specifically, $R^5$ represents a hydrogen atom, halogen atom, hydroxy group, methoxy group or 2,6-dioxycyclohexyl group.

In the general formula (I) described above, n is specifically 0, 1, 2 or 3; more specifically 0, 1, or 2, further specifically 0 or 1; and most specifically 0.

Throughout the specification, the "$C_1$-$C_{20}$ hydrocarbon group" refers to a hydrocarbon group which may be saturated or unsaturated acyclic or may also be saturated or unsaturated cyclic and which may be either linear or branched when it is acyclic. Examples of the $C_1$-$C_{20}$ hydrocarbon group include a $C_1$-$C_{20}$ alkyl group, $C_2$-$C_{20}$ alkenyl group, $C_2$-$C_{20}$ alkynyl group, $C_3$-$C_{20}$ allyl group, $C_4$-$C_{20}$ alkyldienyl group, $C_4$-$C_{20}$ polyenyl group, $C_6$-$C_{18}$ aryl group, $C_6$-$C_{20}$ alkylaryl group, $C_6$-$C_{20}$ arylalkyl group, $C_4$-$C_{20}$ cycloalkyl group, $C_4$-$C_{20}$ cycloalkenyl group, ($C_3$-$C_{10}$ cycloalkyl) $C_1$-$C_{10}$ alkyl group, etc.

More specifically, the $C_1$-$C_{20}$ hydrocarbon group used in the present invention includes a $C_1$-$C_{10}$ alkyl group, $C_2$-$C_{10}$ alkenyl group, $C_2$-$C_{10}$ alkynyl group, $C_3$-$C_{10}$ group, $C_4$-$C_{10}$ alkyldienyl group, $C_4$-$C_{10}$ polyenyl group, $C_6$-$C_{10}$ aryl group, $C_6$-$C_{12}$ alkylaryl group, $C_6$-$C_{12}$ arylalkyl group, $C_4$-$C_{10}$ cycloalkyl group, $C_4$-$C_{10}$ cycloalkenyl group, etc.

In the specification, the "alkyl group" refers to an alkyl group which may be linear or branched, and examples include methyl group, ethyl group, propyl group, n-butyl group, t-butyl group, pentyl group, hexyl group, etc.

In the specification, the "alkenyl group" refers to a straight or branched alkenyl group of 2 to 10 carbon atoms having 1 to 3 double bonds. Specific examples include ethenyl, 1-propenyl, 2-propenyl, 1-methylethenyl, 1-butenyl, 2-butenyl, 3-butenyl, 2-methyl-2-propenyl, 1-pentenyl, 2-pentenyl, 4-pentenyl, 3-methyl-2-butenyl, 1-hexenyl, 2-hexenyl, 1-heptenyl, 2-heptenyl, 1-octenyl, 2-octenyl, 1,3-octadienyl, 2-nonenyl, 1,3-nonadienyl, 2-decenyl, etc.

The "alkynyl group" refers to a straight or branched alkynyl group of 2 to 10 carbon atoms having 1 to 3 triple bonds and specific examples include ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl, 2-decynyl, etc.

The "cycloalkyl group" refers to, for example, a cycloalkyl group having 3 to 10 carbon atoms. Specific examples include cyclopropyl, cyclobutyl, cyclopentyl, cyclohexyl, cycloheptyl, etc. The lower cycloalkyl group includes a cycloalkyl group having 3 to 6 carbon atoms.

The "alkoxy group" refers to an oxy group, to which an alkyl group is bound and specifically includes methoxy, ethoxy, propoxy, 2-propoxy, butoxy, 1,1-dimethylethoxy, pentoxy, hexoxy, etc.

The "acyl group" includes, for example, formyl, acetyl, propanoyl, 2-propanyol, pivaloyl, valeryl, pivaloyl, trifluoroacetyl, benzoyl, naphthoyl, nicotinoyl, methanesulfonyl, trifluoromethanesulfonyl, p-toluenesulfonyl, etc.

The "aryl group" includes, for example, phenyl group, a naphthyl group such as 1-naphthyl group, 2-naphthyl group, etc., an indenyl group such as 2-indenyl group, etc., an anthryl group such as 2-anthryl group, etc., a tolyl group such as 2-tolyl group, 3-tolyl group, 4-tolyl group, etc., biphenyl group, and the like.

The "heterocyclic group" includes a 5- to 7-membered saturated heterocyclic group or unsaturated heterocyclic group having, for example, 1 to 3 nitrogen atoms, oxygen atoms and/or sulfur atoms. Examples of the saturated heterocyclic group include tetrahydrofuryl, pyrrolidinyl, pyrazolidinyl, imidazolidinyl, piperidyl, morpholinyl, thiamorpholinyl and piperazinyl. Examples of the unsaturated heterocyclic group include furyl, thienyl, indolyl, isothiazolyl, etc.

The groups which can be optionally substituted on the hydrocarbon group, the heterocyclic group, etc., include, for instance, a halogen atom (e.g., fluorine, chlorine, bromine, iodine, etc.), nitro group, cyano group, a $C_{1-6}$ alkyl group which may optionally be halogenated, a $C_{3-6}$ cycloalkyl group which may optionally be halogenated, a $C_{1-6}$ alkoxy group which may optionally be halogenated, a $C_{1-6}$ alkylthio group which may optionally be halogenated, hydroxy group, amino group, a mono-$C_{1-6}$ alkylamino group (e.g., methylamino group, ethylamino group, propylamino group, isopropylamino group, butylamino group, etc.), a di-$C_{1-6}$ alkylamino group (e.g., dimethylamino group, diethylamino group, dipropylamino group, dibutylamino group, ethylmethylamino group, etc.), formyl group, carboxy group, carbamoyl group, a $C_{1-6}$ alkylcarbonyl group which may optionally be halogenated, a $C_{1-6}$ alkoxycarbonyl group (e.g., methoxy carbonyl group, ethoxy carbonyl group, propoxy carbonyl group, tert-butoxycarbonyl group, etc.), a mono-$C_{1-6}$ alkylcarbamoyl group (e.g., methylcarbamoyl group, ethylcarbamoyl group, etc.), a di-$C_{1-6}$ alkylcarbamoyl group (e.g., dimethylcarbamoyl group, diethylcarbamoyl group, ethylmethylcarbamoyl group, etc.), a $C_{1-6}$ alkylsulfonyl group which may optionally be halogenated, formylamino group, a $C_{1-6}$ alkylcarboxamido group which may optionally be halogenated, a $C_{1-6}$ alkoxycarboxamido group (e.g., methoxycarboxamido group, ethoxycarboxamido group, propoxycarboxamido group, butoxycarboxamido group, etc.), a $C_{1-6}$ alkylsulfonylamino group (e.g., methylsulfonylamino group, ethylsulfonylamino group, etc.), a $C_{1-6}$ alkylcarbonyloxy group (e.g., acetoxy group, propanoyloxy group, etc.), a $C_{1-6}$ alkoxycarbonyloxy group (e.g., methoxycarbonyloxy group, ethoxycarbonyloxy group, propoxycarbonyloxy group, butoxycarbonyloxy group, etc.), a mono-$C_{1-6}$ alkyl-carbamoyloxy group (e.g., methylcarbamoyloxy group, methylcarbamoyloxy group, etc.), a di-$C_{1-6}$ alkylcarbamoyloxy group (e.g., dimethylcarbamoyloxy group, diethylcarbamoyloxy group, etc.) and the like. The number of these substituents to be substituted is not particularly restricted but these substituents are substituted in 1 to 5, specifically in 1 to 3.

Next, the present invention provides a process of producing the isoxazole derivative represented by the following formula (I):

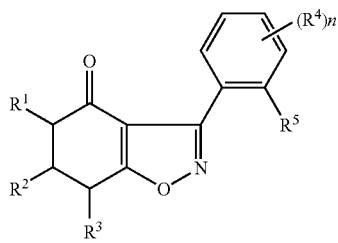

($R^1$ represents a hydrogen atom, optionally substituted $C_1$-$C_{20}$ hydrocarbon group or optionally substituted $C_1$-$C_{10}$ alkoxycarbonyl group;

$R^2$ and $R^3$, which may be the same or different, each independently represents a hydrogen atom, halogen atom, hydroxy group, optionally substituted $C_1$-$C_{20}$ alkyl group, or optionally substituted $C_6$-$C_{20}$ aryl group;

$R^4$, which may be the same or different, each independently represents a hydrogen atom, halogen atom, hydroxy group, cyano group, nitro group, optionally substituted amino group, optionally substituted $C_1$-$C_{20}$ hydrocarbon group, optionally substituted $C_1$-$C_{10}$ alkoxy group, optionally substituted $C_1$-$C_{10}$ acyl group or optionally substituted 5- to 7-membered heterocyclic group;

$R^5$ represents a hydrogen atom, halogen atom, hydroxy group, optionally substituted $C_1$-$C_{20}$ hydrocarbon group or optionally substituted 5- to 7-membered heterocyclic group; and, n represents 0, 1, 2, 3 or 4);

which comprises reacting the compounds represented by the following formula (II):

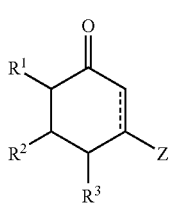

(wherein $R^1$, $R^2$ and $R^3$ are the same as stated above; Z represents $-O^-M^+$ (wherein M represents Na, K or $NEt_3$), oxo or hydroxy group; and the dotted line represents a chemical bond when Z is $-O^-M^+$ or hydroxy group) with the compounds represented by the following formula (III):

(III)

(wherein $R^4$, $R^5$ and n are the same as stated above; and Y represents $-C(X)=NOH$ (wherein X is a halogen atom) or $-CNO$) in the absence of a solvent or in a solvent inert to the reaction.

BEST MODE FOR CARRYING OUT THE INVENTION

Hereinafter, the process of the present invention is described in more detail.

The isoxazole derivatives of the present invention can be produced, e.g., by the process shown by Scheme (I) below.

Scheme (Ia)

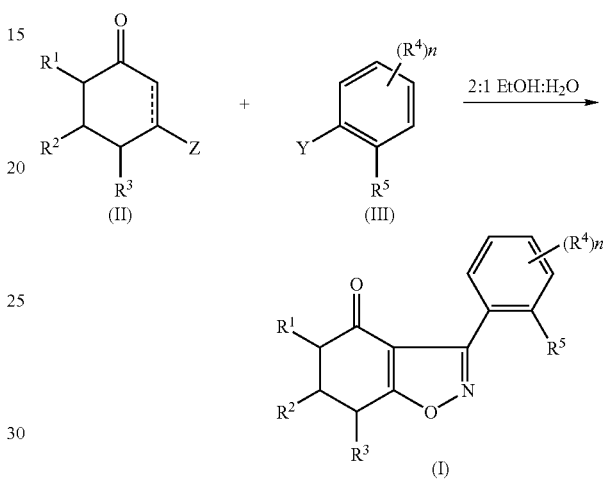

[wherein $R^1$, $R^2$, $R^3$, $R^4$, $R^5$, Z, Y and n have the same significance as described above].

In Scheme (I) described above, the compounds represented by general formula (II) (especially the compound wherein Z is oxo) are reacted with the compounds represented by general formula (III) in the absence of a solvent or in a solvent inert to the reaction; thus, the isoxazole compounds represented by general formula (I) can be produced.

The solvents inert to the reaction which can be used for the reaction described above, include, for instance, an alcohol type solvent such as methanol, ethanol, isopropyl alcohol, etc.; an ethereal solvent such as tetrahydrofuran, diethyl ether, etc.; a halogenated hydrocarbon type solvent such as dichloromethane, chloroform, etc.; an aromatic solvent such as benzene, toluene, etc.; a nitrile type solvent such as acetonitrile, etc.; an amide type solvent such as N,N-dimethylformamide, etc.; a ketone type solvent such as dimethyl ketone, etc.; a sulfoxide type solvent such as dimethyl sulfoxide, etc.; water, and the like. These solvents may be used as an admixture of two kinds or more in an appropriate proportion. In the reaction above, a solvent mixture of an alcohol such as ethanol and water (e.g., 2:1) is preferably used.

The reaction described above is carried out, for example, at a temperature of −78° C. to 150° C., preferably at 10° C. to 80° C. for 0.1 to 144 hours, preferably 0.1 to 72 hours. This reaction is carried out normally under ordinary pressure but, if necessary, can be carried out under reduced pressure or under pressure.

On the other hand, the reaction of the compounds represented by general formula (I) with the compounds represented by general formula (II) can also be carried out in the presence of a catalytic amount of an amine base. Examples of the amine base used herein include an aromatic amine such as pyridine, lutidine, etc.; a tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. More specifically, the tertiary amine such as triethylamine, tripropylamine, tributylamine, cyclohexyldimethylamine, 4-dimethylaminopyridine, N,N-dimethylaniline, N-methylpiperidine, N-methylpyrrolidine, N-methylmorpholine, etc. are preferably employed. The amount of the amine base used is 0.05 to 1.0 mol, preferably 0.1 to 0.5 mol, based on 1 mol of the compound (II).

The reaction is carried out in the absence of a solvent or in a solvent inert to the reaction. The solvents inert to the reaction which can be used in the reaction, include, for example, an alcohol type solvent such as methanol, ethanol, etc.; an ethereal solvent such as tetrahydrofuran, 1,4-dioxan, etc.; a halogenated hydrocarbon type solvent such as dichloromethane, chloroform, etc.; an aromatic solvent such as benzene, toluene, etc.; a nitrile type solvent such as acetonitrile, etc.; an amide type solvent such as N,N-dimethylformamide, etc.; a sulfoxide type solvent such as dimethyl sulfoxide, etc.; 1,2-dimethoxyethane, water, and the like. These solvents may be used as an admixture of two kinds or more in an appropriate proportion. Of these solvents, the alcohol type solvent such as ethanol, etc. is preferably used.

The reaction described above is carried out, for example, at a temperature of −78° C. to 150° C., preferably at 0° C. to 100° C. and more preferably at 20° C. to 80° C. for 0.1 to 50 hours, preferably 1 to 50 hours and more preferably for 1 to 20 hours. This reaction is carried out normally under ordinary pressure but, if necessary, can be carried out under reduced pressure or under pressure.

In these reactions, a molecular sieve, a desiccant or the like can accelerate the reaction. For example, 3 Å molecular sieve, 5 Å molecular sieve, basic alumina, etc. can accelerate these reactions. Therefore, these molecular sieves, desiccants, etc. are added to the reaction mixture in proper quantities.

The desired isoxazole compounds can be obtained from the reaction mixtures thus obtained, if necessary, by means of separation, e.g., various chromatographies, etc.

When $R^1$ is —C(=O)OR$^{1a}$, Z is —O$^-$Na$^+$, and Y is —C(X)=NOH, the compound of formula (I) can be synthesized by the process shown by Scheme (Ib) described below. The reaction conditions are the same as described above.

Scheme (Ib)

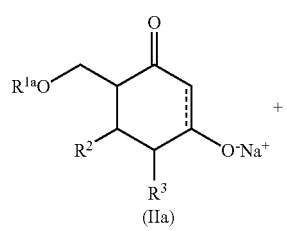

+

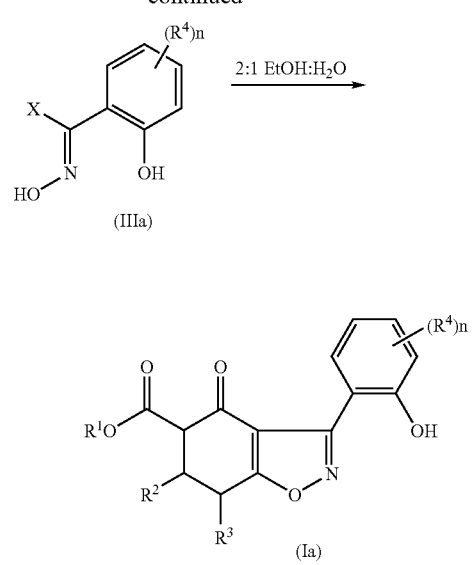

[wherein $R^1$, $R^2$, $R^3$, $R^4$ and n have the same significance as described above.]

According to a preferred embodiment of the present invention, the isoxazole derivatives represented by the following formula (I'):

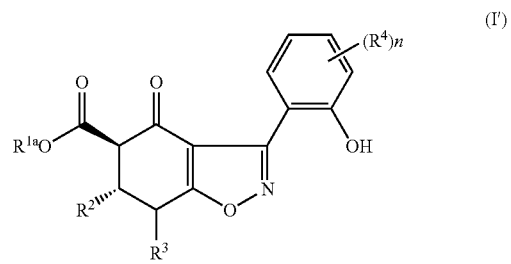

can be obtained.

Next, the compounds represented by formula (II), which are used in Schemes (Ia) and (Ib) described above, are either publicly known or can be synthesized by publicly known methods from publicly known compounds. The compounds represented by formula (IIa) can be synthesized by the process of Scheme (II) described below (e.g., see Edafiogho, I. O., Hinko, C. N., Chang, H., Moore, J. A., Mulzac, D., Nicholson, J. M., Scott, K. R., J. Med. Chem. 1992, 35, 2798-2805).

Scheme (II)

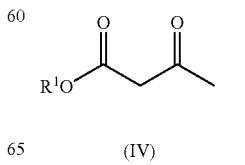

+

-continued

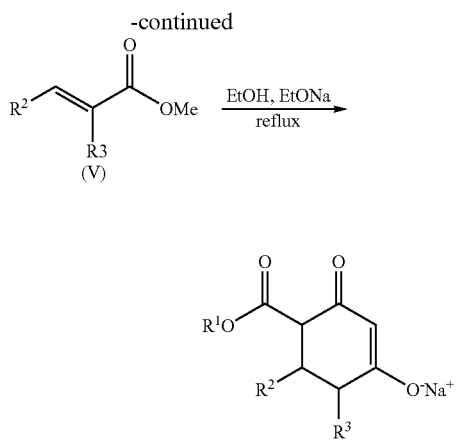

In Scheme (II) above, the compounds represented by general formula (II) can be obtained by reacting the 1,3-dicarbonyl compounds represented by general formula (IV) with the ester compounds represented by general formula (V) in the absence of a solvent or in a solvent inert to the reaction.

The solvents inert to the reaction which can be used for the reaction described above, include, for instance, an alcohol type solvent such as methanol, ethanol, etc.; an ethereal solvent such as tetrahydrofuran, diethyl ether, etc.; a halogenated hydrocarbon type solvent such as dichloromethane, chloroform, etc.; an aromatic solvent such as benzene, toluene, etc.; a nitrile type solvent such as acetonitrile, etc.; an amide type solvent such as N,N-dimethylformamide, etc.; a ketone type solvent such as dimethyl ketone, etc.; a sulfoxide type solvent such as dimethyl sulfoxide, etc.; water, and the like. These solvents may be used as an admixture of two kinds or more in an appropriate proportion. In the reaction above, an alcohol type solvent such as ethanol, etc. is preferably used.

The reaction described above is carried out usually in the presence of a base. Preferred examples of the base which can be used in this reaction are alkali or alkaline earth metal alkoxides such as sodium ethoxide, sodium butoxide, potassium ethoxide, potassium butoxide, etc.

The reaction described above is carried out at a temperature of, for example, −78° C. to 150° C., preferably at 0° C. to 100° C. for 10 minutes to 72 hours, preferably for 30 minutes to 12 hours. Preferably, this reaction can be carried out under reflux at a reflux temperature. This reaction is carried out normally under ordinary pressure but, if necessary, can be carried out under reduced pressure or under pressure.

Next, the compounds represented by formula (IIIa) used in Scheme (Ib) above (the compounds of formula (III) wherein $R^5$ is OH and Y is —C(X)=NOH) are publicly known or can be synthesized from publicly known compounds by publicly known methods. For example, the compounds represented by formula (IIIa) can be synthesized by the process of Scheme (III) described below (e.g., see Larsen, K. E., Torssell, K. B. G., Tetrahedron 1986, 40, 2985).

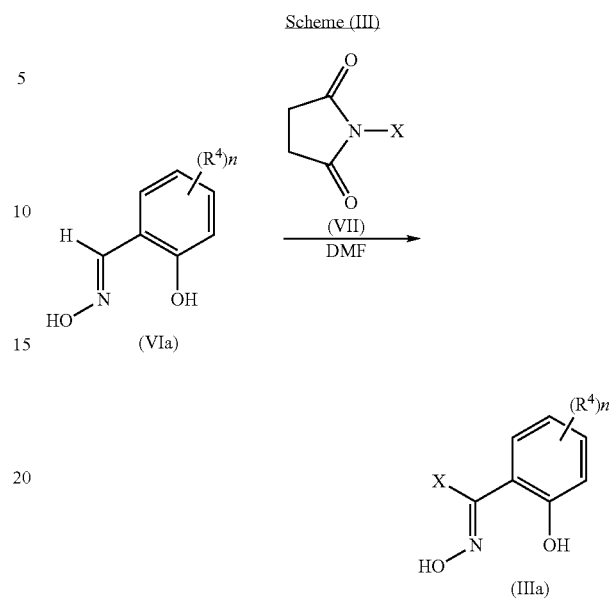

In Scheme (III) described above, the hydroximino compounds represented by general formula (III) can be obtained by halogenating the oxime compound of general formula (VI) with the halogenated imide compounds (X is a halogen atom) represented by general formula (VII) in the absence of a solvent or in a solvent inert to the reaction. In the halogenation any agent is usable so long as it is a safe halogenating agent. Other chlorinating agents used herein include, for example, chlorine, hypochlorous acid, sulfinyl chloride, sulfonyl chloride, etc.

The solvents inert to the reaction which can be used for the reaction described above, include, for example, an alcohol type solvent such as methanol, ethanol, etc.; an ethereal solvent such as tetrahydrofuran, diethyl ether, etc.; a halogenated hydrocarbon type solvent such as dichloromethane, chloroform, etc.; an aromatic solvent such as benzene, toluene, etc.; a nitrile type solvent such as acetonitrile, etc.; an amide type solvent such as N,N-dimethylformamide, etc.; a ketone type solvent such as dimethyl ketone, etc.; water, and the like. These solvents may be used as an admixture of two kinds or more in an appropriate proportion. In the reaction above, the amide type solvent such as N,N-dimethylformamide, etc. is preferably used.

The reaction described above is carried out, for example, at a temperature of −78° C. to 100° C., preferably at −78° C. to −60° C. for 5 minutes to 72 hours, preferaby for 5 minutes to 36 hours.

The isoxazole compounds of the present invention thus obtained can be provided for further reduction, esterification, alkylation, transfer reaction, imine-forming reaction, cyclization, etc. to convert into useful harmaceutical compounds, agricultural chemicals, dye compounds, etc.

EXAMPLES

Hereinafter the present invention is described with reference to EXAMPLES. However, the present invention is not deemed to be limited to EXAMPLES described below.

Example 1

Synthesis of ethyl 3-(2-hydroxyphenyl)-6-methyl-4-oxo4,5,6,7-tetrahydrobenzo [d]isoxazole-5-carboxylate N,2-Dihydroxybenzenecarboximidoyl chloride in 100 mL of ethanol was added to sodium salt of ethyl 2-methyl4,6-dioxocyclohexanecarboxylate in a solvent mixture of 125 mL of water and 75 mL of ethanol at a temperature of 55° C. over an hour. The reaction mixture was maintained at this temperature for 4 hours and then cooled down to room temperature. After diluting with water (100 mL), the mixture was extracted with ethyl acetate (2×100 mL). The resulting extract was washed with saturated sodium chloride aqueous solution (150 mL), dried over anhydrous sodium sulfate, and then concentrated under reduced pressure. The residue was treated with diethyl ether to give the product (2.48 g) as white powders. The residue was further purified by silica gel preparative thin layer chromatography to give additional 2.15 g of the product as white powders (total amount yielded at the 2 steps: 4.63 g, yield: 60%). The physicochemical properties of the compound obtained are shown below.

$^1$H NMR (400 MHz, CDCl$_3$) δ 9.38 (br s), 8.57 (dd, 1H, J=7.9,0.7), 7.38 (t, 1H, J=7.2), 7.07-7.00 (m, 2H), 4.28 (q, 2H, J=7.0), 3.38-3.31 (m, 2H), 2.95-2.89(m, 1H), 2.80 (dd, 1H, J=17.6,9.7), 1.32 (t, 3H, J=7.1), 1.25 (d, 3H, J=6.5)

$^{13}$C NMR (100.5 MHz, CDCl$_3$) δ 187.0, 180.4, 169.0, 159.7, 156.6, 132.7, 131.8, 119.8, 117.3, 113.7, 112.2, 62.6, 61.6, 32.5, 29.7, 19.6, 14.2

IR (thin layer): 3230, 2974, 1739, 1691, 1590, 1428, 1445, 1253, 1023, 751

Elemental Analysis (as C$_{17}$H$_{17}$NO$_5$) Calcd. C, 64.75%; H, 5.43%; N, 4.44% Found C, 64.53%; H, 5.45%; N, 4.25%

Example 2

Synthesis of (±)-3-(2-[1,3]dioxan-2-yl-6-methoxyphenyl)-6-methyl-6,7-dihydro-5H-benzo[d]isoxazol-4-one

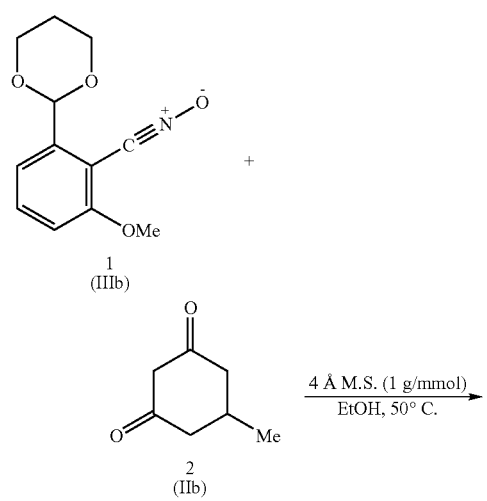

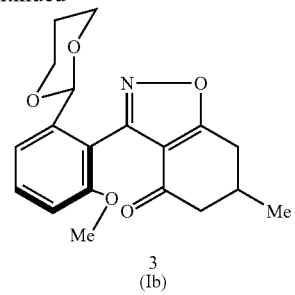

(Step 1)

The compound (IIb) (4.8 mmols, 1.2 equiv) described above was added to the compound (IIIb) (4.0 mmols, 1.0 equiv) described above in 30 mL of isopropyl alcohol at room temperature. Thereafter, powdered 4 Å molecular sieves (4 g, 1 g/mmol) were added to the mixture. The resulting yellow slurry was heated to 50° C. and this temperature was maintained for 36 hours. The mixture was cooled to room temperature, then filtered, concentrated and purified by silica gel column chromatography (1:1 hexane/EtOAc). The compound (Ib) described above was obtained as white foam (3.24 mmols, yield: 81%).

(Step 2)

Triethylamine (NEt$_3$: 2.17 mmols, 1.40 equiv) was added to the compound (IIb) (2.32 mmols, 1.50 equiv) described above in 10 mL of ethanol at room temperature. The solution obtained was warmed at 50° C. and stirred for 24 hours at the temperature. After concentrating under reduced pressure, the concentrate was purified by silica gel column chromatography (1:1 hexane/EtOAc) to give the compound (Ib) described above as white foam (1.36 mmol, yield: 88%).

The physicochemical properties of the compound (Ib) described above are shown below.

$^1$H NMR (400 MHz, CDCl$_3$) δ {1.21 (d, J=6.4 Hz), 1.23 (d, J=6.4 Hz), 3H}, 1.28-1.35 (m, 1H), 2.07-2.18 (m, 1H), 2.21-2.31 (m, 1H), 2.50-2.32 (m, 2H), 2.68-2.77 (m, 1H), 3.15-3.24 (m, 1H), 3.61-3.69 (m, 1H), {3.71 (s), 3.73 s, 3H}, 3.82-3.89 (m, 1H), 3.97-4.05 (m, 1H), 4.14-4.22 (m, 1H), 5.46 (s, 1H), 6.97 (dd, 1H, J=7.4, 4.8 Hz), 7.38 (dd, 1H, J=7.4, 4.8 Hz), 7.47 (t, 1H, J=7.4 Hz)

$^{13}$C NMR (400 MHz, CDCl$_3$) δ 14.1, 15.5*, 20.5, 20.7*, 25.5, 25.7*, 30.2, 30.7*, 30.9, 31.0*, 46.4, 46.6*, 55.8, 55.9*, 60.3, 61.2*, 67.0, 67.1*, 67.1, 67.4*, 99.1, 99.4, 111.1, 111.2*, 112.2, 115.1, 116.0, 116.1*, 118.2, 118.3*, 118.4, 127.2, 130.9, 130.9*, 138.7, 155.6, 155.7*, 157.6, 157.8*, 179.7, 179.9*, 190.3, 190.5* (this compound is present in a mixing ratio of 1:1 as an atropisomer; symbol * indicates the peaks, which became double intensity by the atropisomer.)

IR (thin layer) n 2964, 2884, 1694, 1599, 1479, 1446, 1272, 1075, 995.

Elemental Analysis (as C$_{19}$H$_{21}$NO$_5$) Calcd.: C, 66.46;H, 6.16;N, 4.08;Found: C, 66.16;H, 6.27;N, 4.03.

Examples 3 through 14

The compound of formula (IIIc) described below was reacted with the compound of formula (IIc) described below to give the compound (Ic) of formula described below. In EXAMPLES 3 and 4 and 10 through 14, the reaction was carried out in substantially the same manner as Step 2 of EXAMPLE 2. In EXAMPLES 5 through 9, the reaction was carried out in substantially the same manner as in EXAMPLE 1. The reaction conditions, yields, amounts yielded, etc. are shown in TABLE 1.

TABLE 1

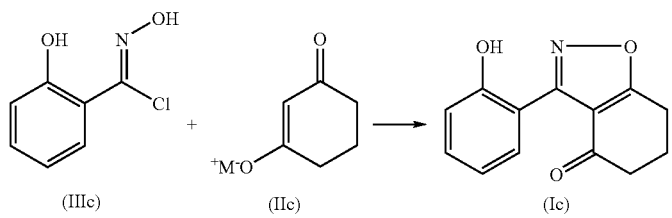

| EX. | M | Solvent | Temp. (° C.) | Amount of the dione (Eq.) | Base (quantity) (Eq.) | Time (min.) | Yield (%) | Amount yielded (mmol) |
|---|---|---|---|---|---|---|---|---|
| 3 | NEt$_3$ | CHCl$_3$ | 60 | 5 | NEt$_3$ (5) | 1080 | <10 | 10.0 |
| 4 | NEt$_3$ | EtOH | 0 | 1.0 | NEt$_3$ (1.0) | 60 | 60 | 1.5 |
| 5 | Na | EtOH | roomtemp. | 2.0 | — | — | 62 | 1.0 |
| 6 | Na | toluene | roomtemp. | 2.0 | — | 15 | 83 | 1.0 |
| 7 | Na | (CF$_3$)$_2$CHOH | roomtemp. | 2.0 | — | 120 | 45 | 1.0 |
| 8 | Na | toluene | roomtemp. | 1.2 | — | 210 | 82 | 1.0 |
| 9 | Na | CH$_2$Cl$_2$ | roomtemp. | 2.0 | — | 20 | 82 | 1.0 |
| 10 | K | toluene | roomtemp. | 2.0 | KHMDS (2.0) | 120 | 35 | 1.0 |
| 11 | Na | toluene | roomtemp. | 2.0 | NaHMDS (2.0) | 60 | 34 | 1.0 |
| 12 | Na | EtOH | roomtemp. | 2.0 | NaOEt (2.0) | 120 | 63 | 1.0 |
| 13 | Na | iPrOH | roomtemp. | 2.0 | NaOiPr (1.8) | 30 | 77 | 1.0 |
| 14 | Na | toluene | roomtemp. | 2.0 | Na$_2$CO$_3$ (2.0) | 480 | 68 | 1.0 |

In the table, Et and iPr represent ethyl and isopropyl, respectively.

Examples 15 through 23

As shown in TABLE 2 below, the compound of formula (IIId) described below was reacted with the compound of formula (IId) described below to give the compound (Id) of formula described below. In these EXAMPLES, the reaction was carried out in substantially the same manner as Step 2 of EXAMPLE 2.

TABLE 2

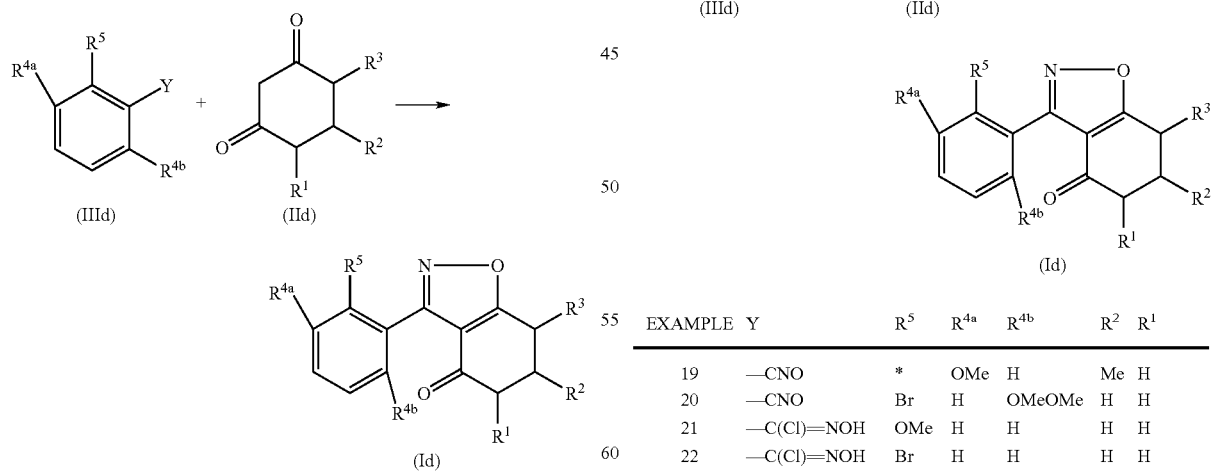

| EXAMPLE | Y | R$^5$ | R$^{4a}$ | R$^{4b}$ | R$^2$ | R$^1$ |
|---|---|---|---|---|---|---|
| 15 | —C(Cl)=NOH | OH | H | H | H | H |
| 16 | —C(Cl)=NOH | OH | H | H | Me | COOEt |
| 17 | —CNO | * | H | OMe | Me | H |
| 18 | —CNO | * | H | OMeOMe | H | H |

TABLE 2-continued

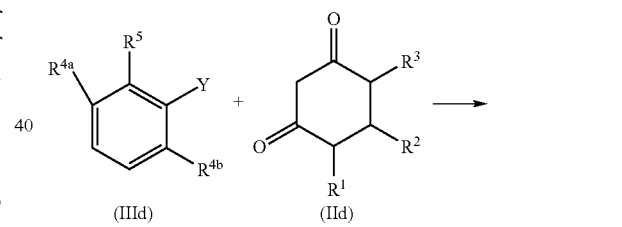

| EXAMPLE | Y | R$^5$ | R$^{4a}$ | R$^{4b}$ | R$^2$ | R$^1$ |
|---|---|---|---|---|---|---|
| 19 | —CNO | * | OMe | H | Me | H |
| 20 | —CNO | Br | H | OMeOMe | H | H |
| 21 | —C(Cl)=NOH | OMe | H | H | H | H |
| 22 | —C(Cl)=NOH | Br | H | H | H | H |
| 23 | —C(Cl)=NOH | H | OMe | H | H | H |

In the table, *, Me and Et represent 2,6-dioxycyclohexanyl, methyl and ethyl, respectively.

The reaction conditions, yields, amounts yielded, etc. are shown in TABLE 3.

TABLE 3

| EX. | Solvent | Temp. (°C.) | Amount of the dione (Eq.) | Base (quantity) (Eq.) | Time (min.) | Yield (%) | Amount yielded (mmol) |
|---|---|---|---|---|---|---|---|
| 15 | iPrOH | room temp. | 2.0 | NaOiPr (1.8) | 30 | 77 | 1.0 |
| 16 | toluene | room temp. | 2.0 | Na (-) | 35 | 70 | 1.0. |
| 17 | EtOH | 50° C. | 1.5 | NEt₃ (1.5) | 1440 | 89 | 1.55 |
| 18 | EtOH | 50° C. | 1.5 | NEt₃ (1.5) | 2160 | 76 | 0.6 |
| 19 | iPrOH | 50° C. | 1.5 | NaOiPr (1.4) | 1440 | 81 | 1.0 |
| 20 | iPrOH | room temp. | 1.3 | NEt₃ (1.2) | 1140 | 79 | 0.5 |
| 21 | iPrOH | room temp. | 2.0 | NaOiPr (2.0) | 30 | 70 | 5.0 |
| 22 | iPrOH | room temp. | 2.0 | NaOiPr (2.0) | 5 | 62 | 1.0 |
| 23 | iPrOH | room temp. | 2.0 | NaOiPr (2.0) | 35 | 64 | 1.0 |

In the table, Et and iPr represent ethyl and isopropyl, respectively.

INDUSTRIAL APPLICABILITY

According to the present invention, there can be provided intermediates useful for synthesis of pharmaceutical compounds, agricultural chemicals, dye compounds, etc. having an isoxazole skeleton and a process of producing the same.

The invention claimed is:

1. An isoxazole derivative represented by the following formula (I')

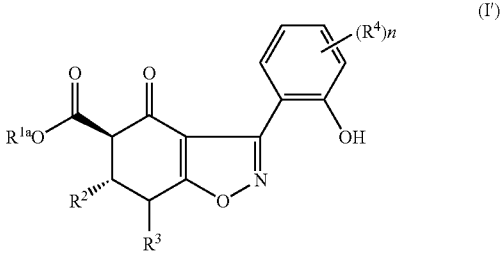

(wherein $R^{1a}$ is an optionally substituted $C_1$-$C_{10}$ alkyl group, optionally substituted $C_2$-$C_{10}$ alkenyl group or optionally substituted $C_2$-$C_{10}$ alkynyl group);

$R^2$ and $R^3$, which may be the same or different, each independently represents a hydrogen atom, halogen atom, hydroxy group, optionally substituted $C_1$-$C_{20}$ alkyl group, or optionally substituted $C_6$-$C_{20}$ aryl group;

$R^4$, which may be the same or different, each independently represents a hydrogen atom, halogen atom, hydroxy group, cyano group, nitro group, optionally substituted amino group, optionally substituted $C_1$-$C_{20}$ hydrocarbon group, optionally substituted $C_1$-$C_{10}$ alkoxy group, optionally substituted $C_1$-$C_{10}$ acyl group or optionally substituted 5- to 7-membered heterocyclic group; and n represents 0, 1, 2, 3 or 4).

* * * * *

UNITED STATES PATENT AND TRADEMARK OFFICE
CERTIFICATE OF CORRECTION

PATENT NO.         : 7,342,036 B2                                    Page 1 of 1
APPLICATION NO.    : 10/932856
DATED              : March 11, 2008
INVENTOR(S)        : Keisuke Suzuki et al.

It is certified that error appears in the above-identified patent and that said Letters Patent is hereby corrected as shown below:

Title page, item [73]

In the Assignee City:

Please insert --Saitama--

Signed and Sealed this

Nineteenth Day of August, 2008

JON W. DUDAS
*Director of the United States Patent and Trademark Office*